(12) United States Patent
Hassan et al.

(10) Patent No.: US 8,034,972 B2
(45) Date of Patent: Oct. 11, 2011

(54) SYSTEM AND PROCESS FOR PRODUCTION OF TOLUENE DIISOCYANATE

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 337 days.

(21) Appl. No.: 12/141,198

(22) Filed: Jun. 18, 2008

(65) Prior Publication Data

US 2009/0005589 A1 Jan. 1, 2009

Related U.S. Application Data

(60) Provisional application No. 60/946,473, filed on Jun. 27, 2007.

(51) Int. Cl.
*C07C 240/00* (2006.01)
(52) U.S. Cl. .......................... 560/359; 560/347; 560/352
(58) Field of Classification Search .................. None
See application file for complete search history.

(56) References Cited

U.S. PATENT DOCUMENTS

| | | | |
|---|---|---|---|
| 3,781,320 A * | 12/1973 | Irwin et al. .................... 560/347 |
| 5,599,968 A | 2/1997 | Bankwitz et al. | |
| 5,877,350 A | 3/1999 | Langer et al. | |
| 6,241,472 B1 * | 6/2001 | Bosch et al. ............... 415/208.3 |
| 6,368,366 B1 | 4/2002 | Langer et al. | |
| 6,368,367 B1 | 4/2002 | Langer et al. | |
| 6,383,237 B1 * | 5/2002 | Langer et al. .................. 44/301 |
| 6,866,411 B1 * | 3/2005 | Stelzer et al. ................ 366/136 |
| 7,461,970 B2 | 12/2008 | Brown | |
| 2003/0043690 A1 | 3/2003 | Holl | |
| 2004/0052158 A1 | 3/2004 | Holl | |
| 2005/0033069 A1 | 2/2005 | Holl et al. | |
| 2006/0041166 A1 | 2/2006 | Stuart | |
| 2008/0144431 A1 * | 6/2008 | Troxler ...................... 366/164.1 |
| 2009/0323458 A1 | 12/2009 | Fischer et al. | |

FOREIGN PATENT DOCUMENTS

GB 1255637 A 12/1971

OTHER PUBLICATIONS

International Search Report, International Application No. PCT/US2008/067835, dated Jan. 12, 2009.
Office Action Dated Jul. 28, 2010 for U.S. Appl. No. 12/635,433.

* cited by examiner

*Primary Examiner* — Sudhakar Katakam
(74) *Attorney, Agent, or Firm* — Porter Hedges LLP; Timothy S. Westby

(57) ABSTRACT

A method for producing toluene diisocyanate is disclosed which comprises forming a dispersion comprising phosgene gas bubbles dispersed in toluene diamine liquid phase, wherein said gas bubbles have a mean diameter less than 1 micron; and subjecting the dispersion to phosgenation reaction conditions, whereby at least a portion of the toluene diamine is phosgenated to form toluene diisocyanate. A system for carrying out the phosgenation of toluene diamine is also disclosed.

9 Claims, 2 Drawing Sheets

US 8,034,972 B2

SYSTEM AND PROCESS FOR PRODUCTION OF TOLUENE DIISOCYANATE

CROSS-REFERENCE TO RELATED APPLICATIONS

This application claims the benefit under 35 U.S.C. §119(e) of U.S. Provisional Patent Application No. 60/946,473 filed Jun. 27, 2007, the disclosure of which is hereby incorporated herein by reference.

STATEMENT REGARDING FEDERALLY SPONSORED RESEARCH OR DEVELOPMENT

Not Applicable.

TECHNICAL FIELD

The present invention generally relates to the liquid/gas phase reaction of toluene diamine and phosgene gas to produce toluene diisocyanate, and more particularly to apparatus and methods for producing toluene diisocyanate. The invention pertains still more particularly to such apparatus and methods which employ high shear mixing of the reactants.

BACKGROUND

Toluene diisocyanate (TDI) is produced today primarily as a chemical feed stock for reaction with polyols to form polyurethanes. One way in which toluene diisocyanate is conventionally made includes (1) nitration, which involves the reaction of toluene with nitric acid and a catalyst to form dinitrotoluene; (2) hydrogenation, in which dinitrotoluene is reacted with hydrogen and a catalyst to form a mixture of isomers of toluene diamine (TDA); (3) distillation of the TDA mixture to produce meta-TDA; and (4) phosgenation, in which the meta-TDA is reacted with phosgene to form a crude TDI mixture. The crude TDI mixture can then be distilled to isolate various molar ratios of TDI isomers, such as an 80:20 mixture of 2,4-TDI and 2,6-TDI, known as TDI (80/20). In some instances the pure 2,4-TDI and a 65:35 mixture of 2,4-TDI and 2,6-TDI, known as TDI (65/35) are isolated. Each of the isocyanate functional groups in TDI can react with a hydroxyl group to form a urethane linkage. Existing processes and production facilities for producing the toluene diisocyanate mixture, in particular, are subject to various constraints such as mass flow limitations, product yield, plant size and energy consumption. Accordingly, there is continuing interest in improving the way that toluene diisocyanate is produced.

SUMMARY OF THE INVENTION

In accordance with certain embodiments of the invention, a method for producing toluene diisocyanate is provided which includes forming a dispersion comprising phosgene gas bubbles dispersed in a toluene diamine liquid phase. The dispersed gas bubbles have a mean diameter less than 1 micron. The method also includes subjecting the dispersion to phosgenation reaction conditions, whereby at least a portion of the toluene diamine is phosgenated to form toluene diisocyanate. In some embodiments, the phosgenation reaction conditions comprise a pressure less than about 600 kPa and a temperature less than about 200° C.

Also provided in accordance with certain embodiments of the invention is a system comprising at least one high shear mixing device configured for producing a dispersion of phosgene gas bubbles in a toluene diamine liquid phase, wherein the resulting dispersion has a mean bubble diameter of less than one micron; a pump configured for delivering a liquid stream comprising toluene diamine to the high shear mixing device; and a vessel configured for receiving the resulting dispersion from the high shear mixing device and for maintaining a predetermined pressure and temperature. In some embodiments the high shear mixing device comprises a rotor/stator set having a rotor tip, the device being configured for operating at a flow rate of at least 300 L/h and tip speed of at least 22.9 m/sec. These and other embodiments and advantages will be apparent in the following detailed description and drawings.

DETAILED DESCRIPTION OF THE PREFERRED EMBODIMENTS

The present system and method for the production of toluene diisocyanate via liquid/gas phase phosgenation of toluene diamine employs an external high shear mechanical device to provide rapid contact and mixing of the chemical ingredients in a controlled environment in a high shear mixing device and/or reactor. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants. Contact time for the reactants and/or catalyst is often controlled by mixing which provides contact with two or more reactants involved in a chemical reaction. A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

System for Production of Toluene Diisocyanate.

Figure 1:
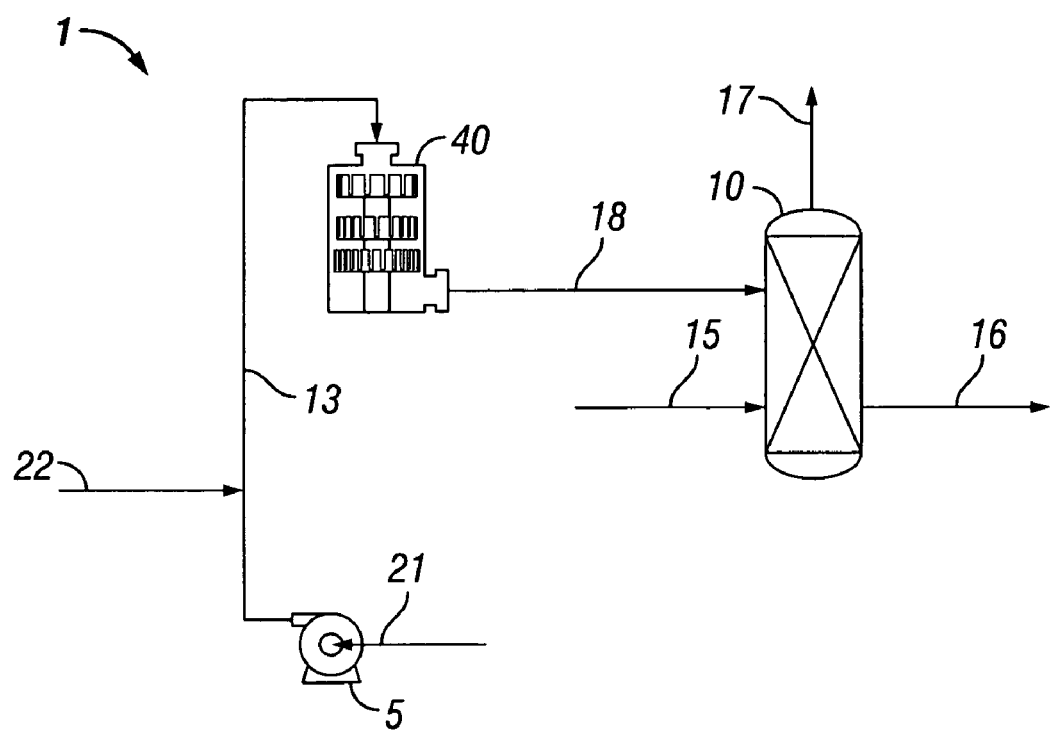
FIG. 1 is a process flow diagram of a process for production of toluene diisocyanate, according to certain embodiments of the invention.

A high shear production system will now be described in relation to FIG. 1, which is a process flow diagram of an embodiment of a high shear system 1 for the production of toluene diisocyanate via phosgenation of toluene diamine. The basic components of a representative system include external high shear mixing device (HSD) 40, vessel 10, and pump 5. As shown in FIG. 1, the high shear device is located external to vessel/reactor 10. Each of these components is further described in more detail below. Line 21 is connected to pump 5 for introducing a liquid stream of toluene diamine. Line 13 connects pump 5 to HSD 40, and line 18 connects HSD 40 to vessel 10. Line 22 is connected to line 13 for introducing phosgene gas into the stream of toluene diamine. Line 17 is connected to vessel 10 for removal of unreacted phosgene gas, toluene diamine vapor, and other reaction gases. Additional components or process steps may be incorporated between vessel 10 and HSD 40, or ahead of pump 5 or HSD 40, if desired. For example, line 16 may be connected to line 21 or line 13, to provide for multi-pass operation, if desired.

High Shear Mixing Device. External high shear mixing device (HSD) 40, also sometimes referred to as a high shear mixer, is configured for receiving an inlet stream via line 13, comprising toluene diamine and phosgene gas. Alternatively, HSD 40 may be configured for receiving the liquid and gaseous reactant streams via separate inlet lines (not shown). Although only one high shear device is shown in FIG. 1, it should be understood that some embodiments of the system may have two or more high shear mixing devices arranged either in series or parallel flow. HSD 40 is a mechanical device that utilizes one or more generators comprising a rotor/stator combination, each of which having a fixed gap between the stator and rotor. HSD 40 is configured in such a way that it is capable of producing submicron (i.e., less than 1 micron in diameter) and micron-sized bubbles in a reactant mixture flowing through the mixer. The high shear mixer comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the 0-1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills, which are classified as intermediate energy devices. A typical colloid mill configuration includes a conical or disk rotor that is separated from a complementary, liquid-cooled stator by a closely-controlled rotor-stator gap, which is commonly between 0.0254-10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

An approximation of energy input into the fluid (kW/L/min) can be estimated by measuring the motor energy (kW) and fluid output (L/min). Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (in meters, for example) times the frequency of revolution (in revolutions per minute). A colloid mill, for example, may have a tip speed in excess of 22.9 m/sec (4500 ft/min) and may exceed 40 m/sec (7900 ft/min). For the purposes of this disclosure, the term "high shear" refers to mechanical rotor stator devices (e.g., colloid mills or rotor/stator mixers) that are capable of tip speeds in excess of 5.1 m/sec. (1000 ft/min) and require an external mechanically driven power device to drive energy into the stream of materials to be reacted. For example, in HSD 40, a tip speed in excess of 22.9 m/sec (4500 ft/min) is achievable, and may exceed 40 m/sec (7900 ft/min). In some embodiments, HSD 40 is capable of delivering at least 300 L/h with a power consumption of about 1.5 kW at a nominal tip speed of at least 22.9 m/sec (4500 ft/min).

HSD 40 combines high tip speeds with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases these local pressure and temperature elevations may persist for nano or pico seconds. In some embodiments, the energy expenditure of the high shear mixer is greater than 1000 W/m$^3$. In embodiments, the energy expenditure of HSD 40 is in the range of from about 3000 W/m$^3$ to about 7500 W/m$^3$. The shear rate is the tip speed divided by the shear gap width (minimal clearance between the rotor and stator). The shear rate generated in HSD 40 may be greater than 20,000 s$^{-1}$. In some embodiments the shear rate is at least 1,600,000 s$^{-1}$. In embodiments, the shear rate generated by HSD 40 is in the range of from 20,000 s$^{-1}$ to 100,000 s$^{-1}$. For example, in one application the rotor tip speed is about 40 m/sec (7900 ft/min) and the shear gap width is 0.0254 mm (0.001 inch), producing a shear rate of 1,600,000 s$^{-1}$. In another application the rotor tip speed is about 22.9 m/sec (4500 ft/min) and the shear gap width is 0.0254 mm (0.001 inch), producing a shear rate of about 901,600 s$^{-1}$.

HSD 40 is capable of highly dispersing or transporting phosgene gas into a main liquid phase comprising toluene diamine at conditions such that at least a portion of the phosgene reacts with the toluene diamine to produce a product stream comprising toluene diisocyanate. In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the DISPAX REACTOR® of IKA® Works, Inc. Several models are available having various inlet/outlet connections, horsepower, nominal tip speeds, output rpm, and nominal flow rate. Selection of a particular device will depend on specific throughput requirements for the intended application, and on the desired bubble size in the outlet dispersion from the high shear mixer.

The high shear device comprises at least one revolving element that creates the mechanical force applied to the reactants. The high shear device comprises at least one stator and at least one rotor separated by a clearance. For example, the rotors may be conical or disk shaped and may be separated from a complementary-shaped stator; both the rotor and stator may comprise a plurality of circumferentially-spaced teeth. In some embodiments, the stator(s) are adjustable to obtain the desired gap between the rotor and the stator of each generator (rotor/stator set). Grooves in the rotor and/or stator may change directions in alternate stages for increased turbulence. Each generator may be driven by any suitable drive system configured for providing the necessary rotation.

In some embodiments, the minimum clearance between the stator and the rotor is in the range of from about 0.0254 mm to about 3.175 mm (about 0.001 inch to about 0.125 inch). In certain embodiments, the minimum clearance between the stator and rotor is about 1.524 mm (0.060 inch). In certain configurations, the minimum clearance between the rotor and stator is at least 1.778 mm (0.07 inch). The shear rate produced by the high shear mixer may vary with longitudinal position along the flow pathway. In some embodiments, the rotor is set to rotate at a speed commensurate with the diameter of the rotor and the desired tip speed. In some embodiments, the colloidal mill has a fixed clearance between the stator and rotor. Alternatively, the colloid mill has adjustable clearance.

In some embodiments, HSD 40 comprises a single stage dispersing chamber (i.e., a single rotor/stator combination, a single generator). In some embodiments, high shear device 40 is a multiple stage inline disperser and comprises a plurality of generators. In certain embodiments, HSD 40 comprises at least two generators. In other embodiments, high shear device 40 comprises at least 3 high shear generators. In some embodiments, high shear device 40 is a multistage mixer whereby the shear rate (which varies proportionately with tip speed and inversely with rotor/stator gap) varies with longitudinal position along the flow pathway, as further described herein below.

In some embodiments, each stage of the external high shear device has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size. In some embodiments, each of the stages is operated with super-fine generator. In some embodiments, at least one of the generator sets has a rotor/stator minimum clearance of greater than about 5.08 mm (0.20 inch). In some embodiments, at least one of the generator sets has a minimum rotor/stator clearance of greater than about 1.778 mm (0.07 inch). In some embodiments the rotors are 60 mm and the stators are 64 mm in diameter, providing a clearance of about 4 mm.

Figure 2:
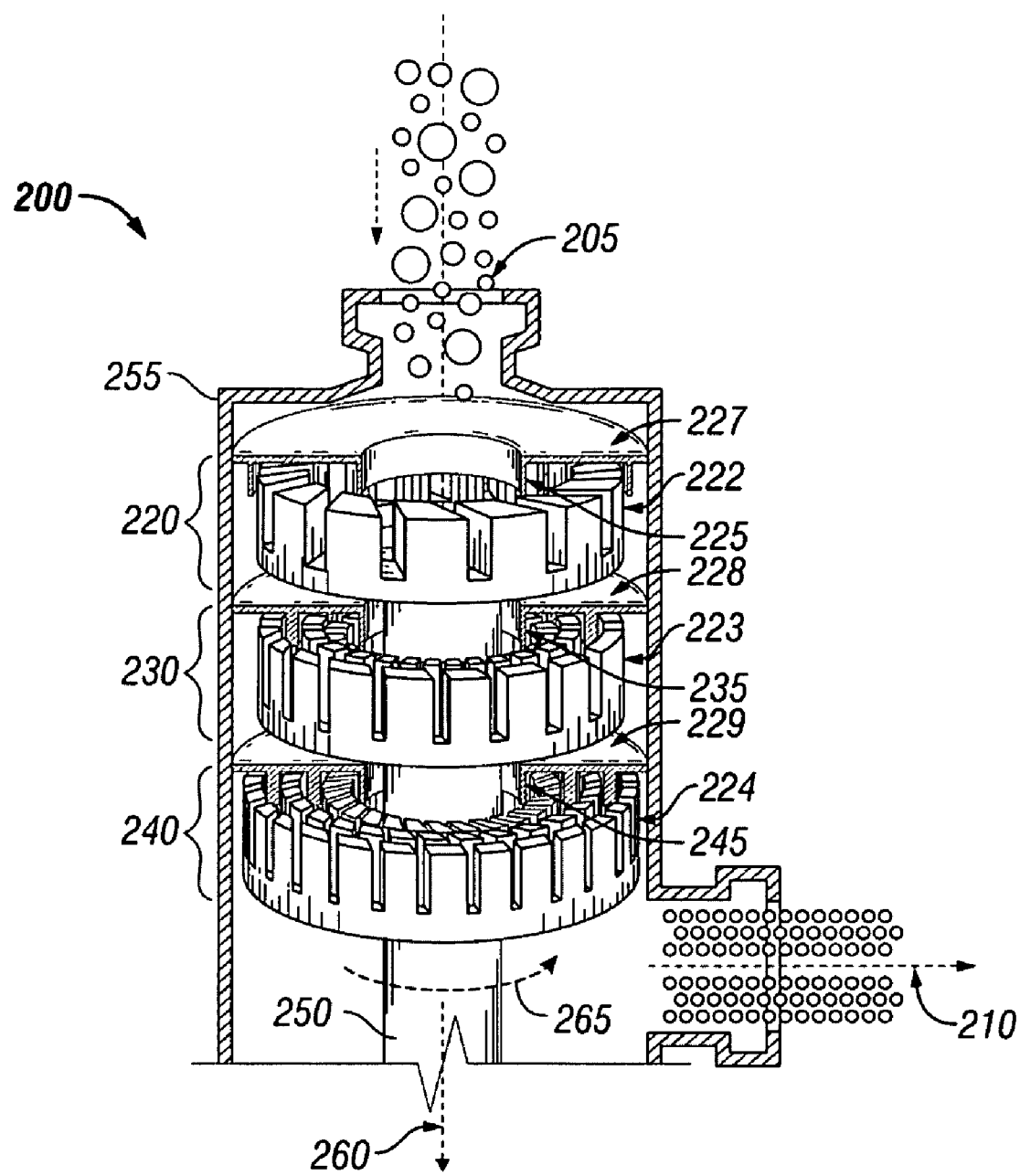
FIG. 2 is a longitudinal cross-section view of a multi-stage high shear device, as employed in an embodiment of the system of FIG. 1.

Referring now to FIG. 2, there is presented a longitudinal cross-section of a suitable high shear device 200. High shear device 200 is a dispersing device comprising three stages or rotor-stator combinations, 220, 230, and 240. Three rotor/stator sets or generators 220, 230, and 240 are aligned in series along drive input 250. The first generator 220 comprises rotor 222 and stator 227. The second generator 230 comprises rotor 223, and stator 228; the third generator 240 comprises rotor 224 and stator 229. For each generator the rotor is rotatably driven by input 250 and rotates, as indicated by arrow 265, about axis 260. Stator 227 is fixedly coupled to high shear device wall 255. Each generator has a shear gap which is the distance between the rotor and the stator. First generator 220, comprises a first shear gap 225; second generator 230 comprises a second shear gap 235; and third generator 240 comprises a third shear gap 245. In some embodiments, shear gaps 225, 235, 245 are between about 0.025 mm and 10.0 mm wide. In some embodiments, the process comprises utilization of a high shear device 200 wherein the gaps 225, 235, 245 are between about 0.5 mm and about 2.5 mm. In certain instances the gap is maintained at about 1.5 mm. Alternatively, the gaps 225, 235, 245 are different for generators 220, 230, 240. In certain instances, the gap 225 for the first generator 220 is greater than about the gap 235 for the second generator 230, which is in turn greater than about the gap 245 for the third generator. As mentioned above, the generators of each stage may be interchangeable, offering flexibility.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. Rotors 222, 223, and 224 may comprise a number of rotor teeth circumferentially spaced about the circumference of each rotor. Stators 227, 228, and 229 may comprise a complementary number of stator teeth circumferentially spaced about the circumference of each stator. In embodiments, the inner diameter of the rotor is about 11.8 cm. In embodiments, the outer diameter of the stator is about 15.4 cm. In certain embodiments, each of three stages is operated with a super-fine generator, comprising a shear gap of between about 0.025 mm and about 3 mm. For applications in which solid particles are to be sent through high shear device 200, shear gap width may be selected for reduction in particle size and increase in particle surface area. In some embodiments, the disperser is configured so that the shear rate will increase stepwise longitudinally along the direction of the flow. The IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2 HP power, output speed of 7900 rpm, flow capacity (water) approximately 300-700 L/h (depending on generator), a tip speed of from 9.4-41 m/sec (1850 ft/min to 8070 ft/min).

Vessel. Vessel or reactor 10 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 10 may be a tower reactor, and in others a tubular reactor or multi-tubular reactor. At least one inlet line 15 may be connected to vessel 10 for introducing additional toluene diamine or phosgene, solvent, or other material, during operation of the system, if desired.

Vessel 10 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 40 in some embodiments, vessel 10 may serve primarily as a storage vessel in some cases. Although generally less desired, in some applications vessel 10 may be omitted, particularly if multiple high shear mixers/reactors are employed in series, as further described below.

Heat Transfer Devices. In addition to the above-mentioned heating/cooling capabilities of vessel 10, other external or internal heat transfer devices for heating or cooling a process stream are also contemplated in variations of the embodiments illustrated in FIG. 1. Some suitable locations for one or more such heat transfer devices are between pump 5 and HSD 40, between HSD 40 and vessel 10, and between vessel 10 and pump 5 when system 1 is operated in multi-pass mode. Some non-limiting examples of such heat transfer devices are shell, tube, plate, and coil heat exchangers, as are known in the art.

Pumps. Pump 5 is configured for either continuous or semi-continuous operation, and may be any suitable pumping device that is capable of providing greater than 203 kPa (2 atm) pressure, preferably greater than 304 kPa (3 atm) pressure, to allow controlled flow through HSD 40 and system 1. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of the pump comprise stainless steel. In some embodiments of the system, pump 5 is capable of pressures greater than about 2027 kPa (20 atm). In addition to pump 5, one or more additional, high pressure pump (not shown) may be included in the system illustrated in FIG. 1. For example, a booster pump, which may be similar to pump 5, may be included between HSD 40 and vessel 10 for boosting the pressure into vessel 10. As another example, a supplemental feed pump, which may be similar to pump 5, may be included for introducing additional reactants into vessel 10. As still another example, a compressor type pump may be positioned between line 17 and HSD 40 for recycling unreacted phosgene gas from vessel 10 to an inlet of the high shear device.

Production of Toluene Diisocyanate.

In operation for the production of toluene diisocyanate, a dispersible phosgene gas stream is introduced into system 1 via line 22, and combined in line 13 with a toluene diamine liquid stream. Alternatively, the phosgene gas may be fed directly into HSD 40, instead of being combined with the liquid reactant (i.e., toluene diamine) in line 13. Pump 5 is operated to pump the liquid reactant through line 21, and to build pressure and feed HSD 40, providing a controlled flow throughout high shear mixer (HSD) 40 and high shear system 1. In some embodiments, pump 5 increases the pressure of the toluene diamine stream to greater than 203 kPa (2 atm), preferably greater than about 304 kPa (3 atm). In some embodiments the pressure is about 1013 kPa (10 atm).

After pumping, the gas and liquid reactants are mixed within HSD 40, which serves to create a fine dispersion of the phosgene gas in the toluene diamine. In some embodiments it creates a fine mixture dispersion of the reactants. As used herein, the term "dispersion" refers to a liquefied mixture that contains two distinguishable substances (or phases) that will not readily mix and dissolve together. A dispersion comprises a continuous phase (or matrix), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. The term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

In HSD 40, the phosgene gas and toluene diamine are highly dispersed such that nanobubbles, submicron-sized bubbles, and microbubbles of the gaseous reactants are formed for superior dissolution into solution and enhancement of reactant mixing. For example, disperser IKA® model DR 2000/4, a high shear, three stage dispersing device configured with three rotors in combination with stators, aligned in series, is used to create the dispersion of phosgene gas in the liquid medium comprising toluene diamine (i.e., "the reactants"). The rotor/stator sets may be configured as illustrated in FIG. 2, for example. For some applications, the direction of rotation of the generators may be opposite that shown by arrow 265 (e.g., clockwise or counterclockwise about axis of rotation 260). The combined reactants enter the high shear mixer via line 13 and enter a first stage rotor/stator combination having circumferentially spaced first stage shear openings. In some applications, the direction of flow of the reactant stream entering inlet 205 corresponds to the axis of rotation 260. The coarse dispersion exiting the first stage enters the second rotor/stator stage, having second stage shear openings. The reduced bubble-size dispersion emerging from the second stage enters the third stage rotor/stator combination having third stage shear openings. The dispersion exits the high shear mixer via line 18. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear mixer includes a PTFE seal, for example, the seal may be cooled using any suitable technique that is known in the art. For example, the reactant stream flowing in line 13 may be used to cool the seal and in so doing be preheated as desired prior to entering the high shear mixer.

The rotor of HSD 40 is set to rotate at a speed commensurate with the diameter of the rotor and the desired tip speed. As described above, the high shear mixer (e.g., colloid mill) has either a fixed clearance between the stator and rotor or has adjustable clearance. HSD 40 serves to intimately mix the gas and the liquid reactants. In some embodiments of the process, the transport resistance of the reactants is reduced by operation of the high shear mixer such that the velocity of the reaction is increased by greater than a factor of about 5. In some embodiments, the velocity of the reaction is increased by at least a factor of 10. In some embodiments, the velocity is increased by a factor in the range of about 10 to about 100 fold. In some embodiments, HSD 40 delivers at least 300 L/h with a power consumption of 1.5 kW at a nominal tip speed of at least 22.9 m/sec (4500 ft/min), and which may exceed 40 m/sec (7900 ft/min). In some embodiments, the mixture is subjected to a shear rate greater than 20,000 $s^{-1}$.

Although measurement of instantaneous temperature and pressure at the tip of a rotating shear unit or revolving element in HSD 40 is difficult, it is estimated that the localized temperature seen by the intimately mixed reactants is in excess of 500° C. and at pressures in excess of 500 kg/cm$^2$ under cavitation conditions. The high shear mixing results in dispersion of the phosgene gas in micron or submicron-sized bubbles. In some embodiments, the resultant dispersion has an average bubble size less than about 1.5 μm. Accordingly, the dispersion exiting HSD 40 via line 18 comprises micron and/or submicron-sized (i.e., mean diameter less than 1 micron) gas bubbles. In some embodiments, the mean bubble size is in the range of about 0.4 μm to about 1.5 μm. In some embodiments the mean bubble size is less than about 1 micron in diameter. In some embodiments, the mean bubble size is less than about 400 nm, is in the range of about 200 nm to about 400 nm, or is about 100 nm in some cases. In many embodiments, the bubbles are able to remain dispersed at atmospheric pressure for at least 15 minutes.

The phosgenation of toluene diamine will occur whenever suitable time, temperature and pressure conditions exist. In this sense the reaction may occur at any point in the path between HSD 40, vessel 10 and pump 5, as shown in FIG. 1, if the temperature and pressure conditions are favorable. As a result of the intimate mixing of the reactants, a significant portion of the chemical reaction may take place in HSD 40. Once dispersed, the resulting toluene diamine/phosgene dispersion, and any toluene diisocyanate product exits HSD 40 via line 18 and is fed into vessel 10, as illustrated in FIG. 1. Accordingly, in some embodiments, reactor/vessel 10 may be used primarily for heating and separation of volatile reaction products from the toluene diisocyanate product. Alternatively, or additionally, vessel 10 may serve as a primary reaction vessel where most of the toluene diisocyanate product is produced. A discrete vessel/reactor is usually desirable to allow for increased agitation and heating and/or cooling of the bulk reactants, and increased residence time, if applicable. Vessel/reactor 10 may be operated in either continuous or semi-continuous flow mode, or it may be operated in batch mode (e.g., a continuous or semi-continuous stirred tank). The contents of vessel 10 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously. External heating and/or cooling heat transfer devices are employed, as needed, to maintain the desired temperature in vessel 10. The bulk or global operating temperature of the reactants is desirably maintained below their flash points. In some embodiments, the operating conditions of system 1 comprise a temperature in the range of from about 100° C. to about 230° C. In embodiments, the temperature is in the range of from about 160° C. to 180° C. In some embodiments, the reaction temperature in vessel 10, in particular, is in the range of from about 155° C. to about 160° C. In some embodiments, the reaction pressure in vessel 10 is in the range of from about 203 kPa (2 atm) to about 5573 kPa-6080 kPa (55-60 atm). In some embodiments, reaction pressure is in the range of from about 811 kPa (8 atm) to about 1520 kPa (15 atm).

If desired, the dispersion may be further processed prior to entering vessel 10. In vessel 10, toluene diisocyanate production continues. The contents of the vessel are stirred continuously or semi-continuously, the temperature of the reactants is controlled (e.g., using a heat exchanger), and the fluid level inside vessel 10 is regulated using standard techniques. Toluene diisocyanate may be produced either continuously, semi-continuously or batch wise, as desired for a particular application. Any reaction gas that is produced exits reactor 10 via gas line 17. This gas stream may comprise unreacted phosgene gas or toluene diamine vapor, nitrogen, and toluene diisocyanate vapor, for example. The reaction gas removed via line 17 may be further treated, and the components may be recycled, as desired. In some cases, line 17 is connected to line 13 or HSD 40 for returning the unreacted gas (e.g., phosgene gas) to the high shear device using a compressor type pump.

The reaction product stream comprising non-converted liquid toluene diamine, toluene diisocyanate, derivatives and byproducts exits vessel 10 by way of line 16. The toluene diisocyanate may be recovered and further processed or treated as known to those of skill in the art. For instance, it can serve as a feed stock to a process in which it is reacted with polyols to form polyurethanes.

Multiple Pass Operation. In the embodiment shown in FIG. 1, the system is configured for single pass operation, wherein the output from vessel 10 goes directly to further processing for recovery of toluene diisocyanate product. In some embodiments it may be desirable to pass the contents of vessel 10, or a liquid fraction containing unreacted toluene diamine, through HSD 40 during a second pass. In this case, line 16 is connected to line 21, and the recycle stream from vessel 10 is pumped by pump 5 into line 13 and thence into HSD 40. Additional phosgene may be injected via line 22 into line 13, or it may be added directly into the high shear device.

Multiple High Shear Mixing Devices. In some embodiments, two or more high shear devices like HSD 40, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments, where multiple high shear devices are operated in series, vessel 10 may be omitted. When multiple high shear devices are operated in series, additional reactant(s) may be injected into the inlet feed stream of each device. In some embodiments, multiple high shear devices 40 are operated in parallel, and the outlet dispersions therefrom are introduced into one or more vessel 10.

The application of enhanced mixing of the reactants by HSD 40 potentially causes greater phosgenation of toluene diamine in various embodiments of the method. In some embodiments, the enhanced mixing potentiates an increase in throughput of the process stream. In some embodiments, the high shear mixing device is incorporated into an established process, thereby enabling an increase in production (i.e., greater throughput). In contrast to some methods that attempt to increase the degree of phosgenation by simply increasing reactor pressures, the superior dispersion and/or dissolution provided by external high shear mixing may allow in many cases a decrease in overall operating pressure while maintaining or even increasing reaction rate. Without wishing to be limited to a particular theory, it is believed that the level or degree of high shear mixing is sufficient to increase rates of mass transfer and may also produce localized non-ideal conditions that enable reactions to occur that might not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate phosgene and toluene diamine into free radicals, which then form into the toluene diisocyanate product.

In some embodiments the production of toluene diisocyanate product is accelerated. For example, in some embodiments the external high shear device provides enhanced time, temperature and pressure conditions resulting in accelerated chemical reactions between multiphase reactants. In some embodiments a high shear process makes possible a reduction in mass transfer limitations, thereby increasing the reaction rate and enabling a reduction in reactor temperature, a reduction in reactor pressure, a reduction in contact time, and/or an increase in product yield. Some embodiments of the disclosed methods provide for more optimal time, temperature and pressure conditions than are currently used in many other processes for production of toluene diisocyanate, and without the need for large volume reactors and substantial unconverted toluene diamine recovery. In some embodiments, the system and methods described herein make possible the design of a smaller and/or less capital intensive process than previously possible without the use of external high shear mixing device 40. Potential advantages of certain embodiments of the disclosed methods are reduced operating costs and increased production from an existing process. Certain embodiments of the disclosed processes additionally offer the advantage of reduced capital costs for the design of new processes. In embodiments, dispersing phosgene gas in the toluene diamine liquid phase decreases the amount of unreacted toluene diamine in the product stream. Potential benefits of some embodiments of this system and method for the production of toluene diisocyanate include, but are not limited to, faster cycle times, increased throughput, higher conversion, reduced operating costs and reduced capital expense due to the possibility of designing smaller reactors, reduced operating costs and reduced capital expense due to operating the process at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method for producing toluene diisocyanate, the method comprising:
    forming a mixture comprising phosgene gas and liquid toluene diamine;
    introducing the mixture into an external high shear device comprising at least one generator comprising a toothed rotor and a complementarily-shaped stator separated by a shear gap width in the range of from about 0.025 mm to about 10.0 mm to form a dispersion comprising phosgene gas bubbles dispersed in the toluene diamine liquid, wherein the gas bubbles have a mean diameter of less than 1 micron and wherein forming said dispersion comprises subjecting said mixture to a shear rate of greater than 20,000 s$^{-1}$ and a local pressure of at least about 1034.2 MPa at said rotor tip; and
    subjecting the dispersion to phosgenation reaction conditions, whereby at least a portion of said toluene diamine is phosgenated to form product comprising toluene diisocyanate.

2. The method of claim 1, wherein said reaction conditions comprise a pressure less than 600 kPa and a temperature less than 200° C.

3. The method of claim 1, wherein the gas bubbles have a mean diameter less than 400 nm.

4. The method of claim 1, wherein the gas bubbles have a mean diameter of no more than 100 nm.

5. The method of claim 1, wherein said rotor comprises a rotor tip, and wherein forming said dispersion comprises subjecting said phosgene gas and said toluene diamine to high shear mixing at a rotor tip speed of at least 22.9 msec.

6. The method of claim 5, wherein said rotor tip speed is at least 40 m/sec.

7. The method of claim 5, wherein forming said dispersion comprises an energy expenditure of at least 1000 W/m$^3$.

8. The method of claim 1, wherein the velocity of said phosgenation reaction is enhanced at least 5 fold compared to a similar process in which said phosgene and toluene diamine are not subjected to said high shear mixing.

9. The method of claim 1, wherein said product further comprises at least one component selected from the group consisting of unconverted toluene diamine, derivatives and byproducts and wherein the method further comprises recovering toluene diisocyanate from the product.

\* \* \* \* \*